US006854349B2

(12) United States Patent
Brandhorst et al.

(10) Patent No.: US 6,854,349 B2
(45) Date of Patent: Feb. 15, 2005

(54) DEVICE FOR DETERMINING THE END OF THE PROCESSING TIME FOR HARDENING MASSES

(75) Inventors: Gerd Brandhorst, Landsberg (DE); Hermann Nirschl, Seefeld (DE); Mark Peuker, Schondorf (DE); Ingo Wagner, Woerthsee (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 10/312,670

(22) PCT Filed: Oct. 11, 2001

(86) PCT No.: PCT/EP01/11769

§ 371 (c)(1),
(2), (4) Date: Jul. 24, 2003

(87) PCT Pub. No.: WO02/34209

PCT Pub. Date: May 2, 2002

(65) Prior Publication Data
US 2004/0000203 A1 Jan. 1, 2004

(30) Foreign Application Priority Data
Oct. 23, 2000 (DE) .......................... 100 52 548

(51) Int. Cl.$^7$ .......................... G01N 33/00; G01N 11/14
(52) U.S. Cl. .......................... 73/866; 73/54.31; 73/54.32
(58) Field of Search .......................... 73/54.28, 54.29, 73/54.3, 54.31, 54.32, 54.33, 54.34, 54.35

(56) References Cited

U.S. PATENT DOCUMENTS

| | | | | |
|---|---|---|---|---|
| 3,350,922 A | * | 11/1967 | Kim et al. .................. 73/54.28 |
| 3,520,659 A | * | 7/1970 | Steinberg et al. ............. 436/69 |
| 3,741,441 A | * | 6/1973 | Eberle .......................... 222/135 |
| 3,802,605 A | * | 4/1974 | Standlick ..................... 222/134 |
| 4,168,018 A | * | 9/1979 | Zahaykevich ................ 222/82 |
| 4,472,963 A | * | 9/1984 | Gyer et al. ................. 73/54.34 |
| 4,612,800 A | * | 9/1986 | Erian ......................... 73/54.01 |
| 5,017,790 A | | 5/1991 | Kojima |
| 5,063,255 A | | 11/1991 | Hasegawa et al. |
| 5,233,916 A | * | 8/1993 | Butler et al. .................. 99/325 |
| 5,499,745 A | * | 3/1996 | Derian et al. ................ 222/136 |
| 5,799,832 A | * | 9/1998 | Mayo .......................... 222/135 |
| 5,821,407 A | * | 10/1998 | Sekiguchi et al. .......... 73/54.28 |
| 6,058,721 A | * | 5/2000 | Midden et al. ............... 62/136 |
| 6,121,362 A | * | 9/2000 | Wanek et al. ................ 524/448 |
| 6,145,373 A | * | 11/2000 | Tymchuck .................. 73/54.28 |

FOREIGN PATENT DOCUMENTS

| | | |
|---|---|---|
| DE | 2850486 A1 | 6/1980 |
| DE | 3233366 A1 | 9/1983 |
| DE | 3919534 | 12/1990 |
| DE | 9017323 U1 | 4/1992 |
| DE | 19741674 | 3/1999 |
| DE | 29906343 | 8/1999 |
| DE | 19903753 C1 | 10/2000 |
| EP | 0492413 B1 | 7/1992 |
| WO | WO-9600560 A1 | 1/1996 |
| WO | WO-9843727 A1 | 10/1998 |

* cited by examiner

Primary Examiner—Charles D Garber
(74) Attorney, Agent, or Firm—Crowell & Moring LLP

(57) ABSTRACT

A device is provided which determines the end of the processsing time for hardening masses, in particular dental molding masses. The device comprises a display unit and a sensor unit which record the change in at least one of the rheological properties of the mass. A method that can be used with such a device is described.

22 Claims, 1 Drawing Sheet

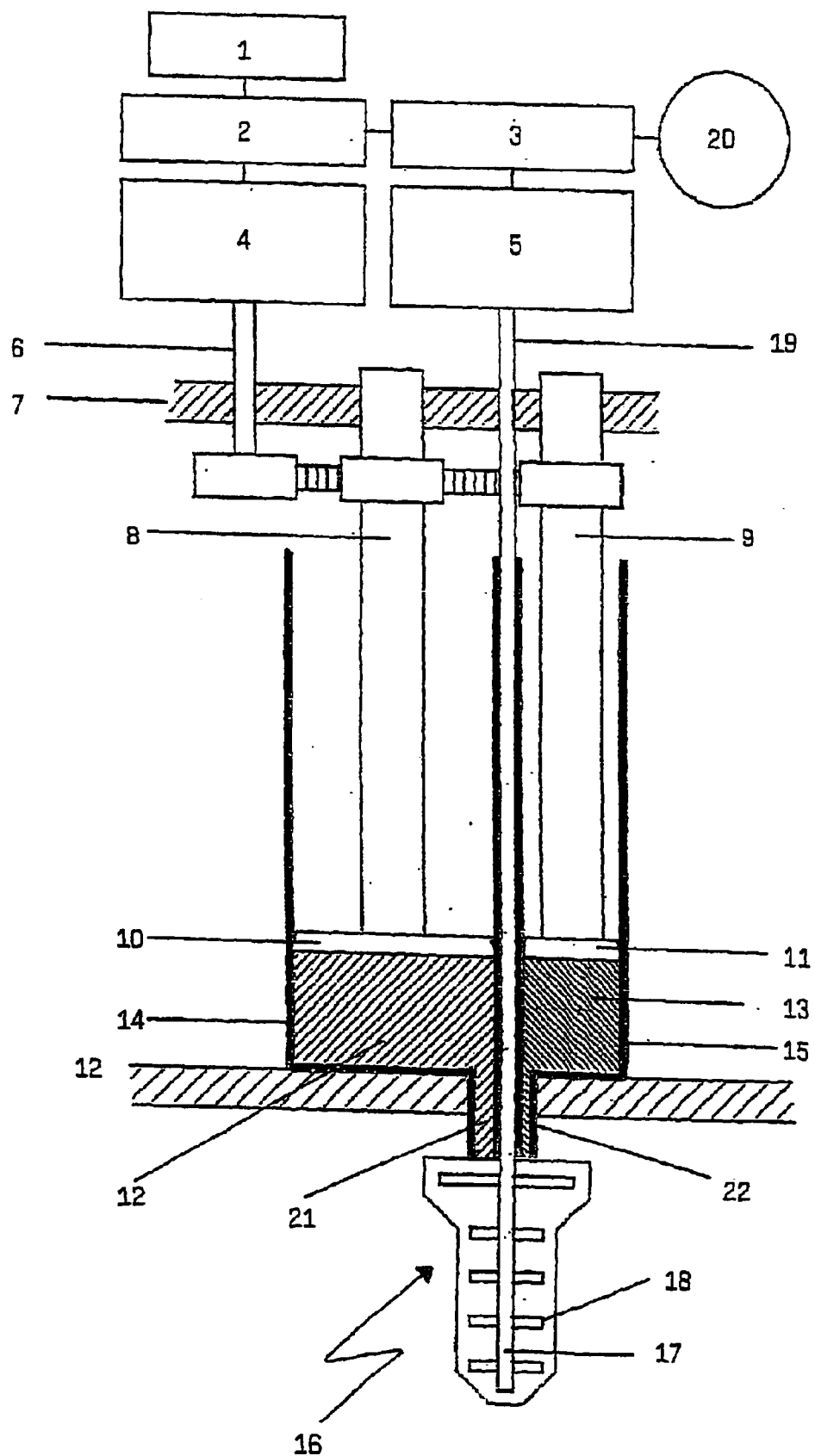

DEVICE FOR DETERMINING THE END OF THE PROCESSING TIME FOR HARDENING MASSES

FIELD OF THE INVENTION

The invention relates to a device and a method for determining the end of the processing time of hardenable compounds, in particular of dental impression compounds.

BACKGROUND AND SUMMARY OF THE INVENTION

To process and use impression compounds in dentistry, the directions for use normally specify suitable times, how the impression compound is to be handled, and when it is to be removed from the patient's mouth.

However, the specified times for processing and the setting behavior of the compounds are subject to various influences in dental practice, such as the actual mouth temperature and room temperature, the mixing energy applied, or the time which was spent on the mixing.

It is conceivable to incorporate indicators into the polymerizable compounds, which indicators are released during the polymerization and indicate the progress of the reaction, for example by a change in the color intensity. Such an attempt is described in WO-96/00560.

A disadvantage of this is that the compounds described contain a further component which may have a negative effect on the desired properties. In clearly definable signal of the setting process and it additionally requires continuous visual monitoring.

DE 29 906 343 U1 attempts to solve the problem by making available a unit for dispensing multi-component compounds, which unit is equipped with a timer clock for specifying a time relevant for the processing.

The unit described has the disadvantage, however, that the mixed compound is again subject to said external influences and, therefore, no clear indication can be given of when the setting process begins.

Moreover, industrial measuring mixers for checking the consistency of cement/water mixtures are known which are used for preparing concrete (DE 199 03 753 C1).

An ancillary device for torque measurement for stirring units, in particular for small-scale fermenters, is described in DE 28 50 486 A1.

DE 39 19 534 A1 discloses a method and a device for preparing bone cement. A propeller is lowered into a vessel in which the bone cement is to be prepared. The preparation of the bone cement is process-controlled.

None of the devices known from the prior art is suitable for determining the change in Theological properties of comparatively quickly hardening compounds, in particular dental impression compounds, which have to be prepared in portions and made available at short intervals one after another.

It is therefore an object of the present invention to propose a device and a method which solve the problems discussed above and inform the user of the progress of the curing of hardening compounds, in particular of dental impression compounds.

This object is achieved by a device and a method as are described below.

The term "setting profile" generally describes the changes in rheological properties occurring during the hardening or setting of hardenable compounds. The determination of the end of the processing time is closely linked to this.

The expression "processing time" is to be understood as the time during which the mixed compound can still be used in the intended manner. In the case of dental impression compounds, this is the time up to which the impression compound can be relatively easily lifted from the article of which an impression is to be made, without appreciably impairing the accuracy of the impression. This is usually the point in time at which the compound changes from the pasty, plastic state to a tough and resilient, rubber-like state.

The expression "hardenable compounds" includes all compounds which, as a result of a polymerization reaction, for example a free-radical, cationic or anionic addition reaction and/or condensation reaction and/or cement reaction, can change from a viscous, flowable, optionally plastically deformable state to a permanently shaped, rigid state.

Compounds whose setting process can preferably be recorded with the device according to the invention usually have the following properties before the start of the setting process. They are pasty, highly viscous substances which rigidify over a period in the range of 0.1 to 60 minutes, preferably 1 to 8 minutes. Before the start of the setting process, such compounds have, for example, a viscosity of class 0 to 3 as determined by the DIN 4823 consistency test, measured with a diameter of less than 80 mm. Materials which may be mentioned as possible examples are silicones, polyethers, epoxy resins and polyurethanes.

The Shore hardness A of the compounds measured according to DIN 53505 fifteen minutes after the end of the processing time usually lies in the range of 20 to 110, preferably in the range of 30 to 80.

The invention is suitable in particular for recording the setting behavior of sealing compounds and dental compounds, preferably dental impression compounds, for example those based on polyethers, A and C silicones, alginates and/or polyether silicones.

"Rheological property" is to be understood as meaning all properties whose change can be recorded via a physical and/or chemical measurement method. These include, in particular, properties such as viscosity, compressive strength, pH, conductivity, dielectric constant, impedance, capacitance, hardness, density and/or temperature.

In contrast to static mixers, the term "dynamic mixer" includes mixers which have at least one rotatably mounted part which is driven via a mixer shaft. Such mixers are described, for example, in DE 90 17 323 U1 or WO-A-98/43727. These mixers are what are referred to as continuous-flow mixers. Mixed material or paste is dispensed from the mixer during the mixing, whereas, during the measurement, the at least partially mixed material remains in the mixer and is not conveyed any further or dispensed.

A dynamic mixer generally comprises the following component parts: a housing, inlet openings, an outlet opening, and a rotatably mounted mixing element with mixing vanes. It is driven either centrally via a rotor which has mixing vanes located on it and rotates in the housing, or externally via a part of the housing serving as rotor and an inner body serving as stator, as is described in DE 19 947 331 A1.

Since mixers of this kind are usually disposable articles whose value is generally considered slight when compared to the substances which are to be mixed, these mixers have a relatively small mixing volume in order to keep the amount of mixed compound to be discarded as small as possible. Such disposable articles are usually made of plastic.

A sensor unit within the meaning of the invention is a unit which is able to record any change in state of the impression compound via a coupling to the mixer shaft. This includes capacitors, ultrasound sensors, pH electrodes, torque transducers, quartz oscillators, thermoelements, current meters, voltage meters, resistance meters, wire strain gages and force transducers.

The term "display unit" includes all units which are able to inform the person using the device of a change in the state of the impression compound, preferably in optical and/or acoustic form. This includes displays, in particular LED displays, and loudspeakers.

The terms "comprise" and "contain" introduce a nonexhaustive list of features. The fact that the word "a" is used before the mention of a feature in the claims does not exclude the possibility that said features can be present more than once, in the sense of "at least one".

The invention has the following advantages:

The device according to the invention and the method according to the invention permit immediate monitoring of the process of hardening of the mixed compound, substantially independently of external influences.

In contrast to measurement mixers, which are known from the prior art, the change in rheological properties is not determined on the basis of a material sample which is subsequently further used, but instead on the basis of a material sample which remains in the mixer and is discarded together with the latter.

The measurement can be carried out directly in the device normally used for mixing and dispensing the hardening compounds. Arranging additional auxiliary means, such as a bypass, chambers, volumetric flask, measurement drives or probes, on known measurement devices is not necessary.

If the measurement takes place from the time at which no further mixed compound is dispensed through the mixer, the invention makes it possible to record the hardening process of the last-mixed compound in the mixer itself, which is usually discarded after the compound has hardened. The information as to when the last-mixed compound begins to harden is, in particular, of not inconsiderable importance to the user, for example the dentist, in preparing an impression of the hard dental tissue using impression compounds.

This represents a decisive advance over the method known from DE 299 06 343 U1, in which the time up to which the compound can be processed is predefined and thus not linked to the actual setting process.

The present invention thus means that dynamic mixers which are used to mix hardening compounds can be used, after the mixing process, to monitor the setting profile of the hardening compounds. The device is not limited to a certain type of mixer. Different mixers with different geometries can be used depending on the compounds which are to be mixed. A mixer can be changed very easily, and this can be done in less than one minute.

The compounds are usually prepared by mixing a base paste and a catalyzer paste. The speed of the setting process differs depending on the mixing ratio and on the substances. However, the device according to the invention is also suitable for determining the setting process of a mixture of three or more pastes or substances. In addition to paste/paste mixtures, the mixtures can also be paste/fluid mixtures or powder/fluid mixtures.

The pastes are mixed in a dynamic mixer, for example according to DE 90 17 323 U or WO-98/43727. This mixer is usually placed on a corresponding cartridge and driven by an electrically actuated mixing unit into which the cartridge can be fitted. Suitable mixing units are described in EP 0 492 413 A.

If the compound obtained by mixing is a dental impression compound, this is preferably used to fill a dental impression tray which is then fitted in a patient's mouth.

Since in this case the setting profile according to the invention is measured outside the mouth and the profile is temperature-dependent, the setting of the compound in the unit takes place somewhat more slowly than in the mouth. This ensures that in every case the compound has completely set before it is removed from the mouth.

The direct correlation between the setting profile in the mouth and in the mixing unit can be determined empirically as a function of the compound used.

The measurement of the change in a rheological property of the hardening compound and the comparison with a predeterminable threshold value are carried out using a measurement program which can be integrated into the control of the mixer shaft or is operated independently of the latter.

The measurement is preferably carried out directly via the mixer shaft of an electrically operated mixing unit, said mixer shaft driving a dynamic mixer. After an impression tray has been filled, the mixer shaft continues to be driven with the forward feed switched off, so that the torque applying on the shaft increases as the compactness of the compound increases. In this embodiment, the end of the processing time of the compound can be indicated by a visual or acoustic signal as soon as a determined threshold value is reached which can be individually set depending on the compound or is automatically set as soon as the cartridge containing the compound is placed in the mixing unit.

The mixer shaft is coupled, for example, to a torque transducer or a rotatable shaft which make it possible to determine the torque applied to the mixer vanes of the mixer or to the mixer shaft, which torque is proportional to the viscosity of the hardening compound. It is also possible to record the change in torque via the current consumption of the drive.

The change is preferably measured with the mixer shaft moving at a reduced speed of rotation compared to during mixing, in order not to unnecessarily introduce rotation energy into the hardening compound, which can lead to an undesirable increase in temperature. This additionally permits a more precise determination of the change. Speeds of rotation which can be used for the mixer shaft during the measurement process lie in the range of $10^0$ to $10^3$ and preferably in the range of $10^1$ to $10^2$ rpm.

In an alternative embodiment, the measurement process takes place via the mixer shaft in a pulsed mode or cyclically. For example, the measurement takes place only every 1, 5 or 10 seconds.

The measurement of the change in a rheological property of the hardening compound can also take place if the mixer shaft does not fully rotate. A turning of the mixer shaft in an angle range of 1 through 180°, preferably 10 through 90°, has proven advantageous.

However, another example of a suitable measuring unit is a quartz oscillator which generates a purely torsional oscillation, the latter being damped by the viscous properties of the hardening compound. The sensor head can be arranged in the form of a probe at or in the area of the tip of the mixer shaft and can be introduced into the compound via a seal in the area of the coupling of dynamic mixer/mixer shaft.

In contrast to measurement mixers known from the prior art, the present device not only allows a hardenable compound to be mixed and delivered, but also makes it possible, after the mixing and delivery process, to determine the setting profile of that part of the mixed compound remaining in the exchangeable, disposable mixer.

A preferred illustrative embodiment is explained below with reference to a FIGURE.

BRIEF DESCRIPTION OF THE DRAWING FIGURE

FIG. 1 shows a diagrammatic representation of a possible arrangement of the individual component parts of the measurement device.

DETAILED DESCRIPTION OF THE DRAWING FIGURE

By pressing the delivery switch (1), the piston motor is activated at a certain speed of rotation (4) via the reciprocating-piston control (2), and the piston motor moves the delivery spindles (8, 9) and the associated pistons (10, 11) forward in the axial direction via the drive shaft (6) and a drive element (7).

The pistons (10, 11) are guided in cartridges (14, 15) which contain the individual components of the hardening compound. By means of the axial movement of the pistons, the two components are pressed through the outlet openings (21, 22) of the cartridges into a dynamic mixer (16).

The mixer-shaft control (3) is activated simultaneously with the activation of the reciprocating-piston control (2) in order to give the mixer-shaft motor the speed of rotation needed for the mixing process, this speed of rotation being transmitted via the mixer shaft (19) to the mixer screw (17) of the dynamic mixer (16). The mixer-shaft control can be activated via the reciprocating-piston control or independently of the latter. The rotating mixing vanes (18) ensure intensive and homogeneous mixing of the two flowing, pasty components (12, 13), so that direct application, for example into an impression tray (not shown here), is possible.

After the impression tray has been completely filled, the delivery switch (1) is released, as a result of which the piston stroke control (2) stops the delivery process. At this moment, the mixer-shaft control (3) switches to measurement mode. In other words, after the mixer-shaft motor (5) has been stationary for 10 seconds, for example, the mixer shaft (19) is rotated through 180°, for example, at a slower and constantly defined speed of rotation for torsion measurement, and the current I required for this is measured.

As soon as the compound located in the mixer (16) begins to harden, the current intensity I needed to keep the mixer shaft at a constant speed of rotation increases proportionally. At a certain state of the hardening compound, a critical threshold value for the current intensity I is exceeded, which threshold value is stored or can be input into the device for the respective compound, with the result that the mixer-shaft control (3) activates the display unit (20), which thereupon outputs an acoustic or visual signal.

What is claimed is:

1. A device for monitoring the setting profile of hardening compounds, comprising:
    a mixer-shaft motor having a control;
    a mixer shaft which may be connected to a dynamic disposable mixer configured for mixing the hardening compound;
    a seat for a cartridge which can be connected to the dynamic disposable mixer which is used to mix the hardening compound;
    a display unit; and
    a sensor unit which can record the change in at least one of the rheological properties of the compound,
    wherein the sensor unit is coupled to the mixer-shaft motor; and
    wherein the disposable mixer cooperates with the sensor unit and is configured to facilitate dispensing a first portion of the hardening compound and measuring the rheological properties of a second portion of the hardening compound remaining in the disposable mixer after the dispensing of the first portion.

2. A device according to claim 1, wherein the rheological properties are chosen from the group consisting of viscosity, compressive strength, pH, conductivity, dielectric constant, impedance, capacitance, hardness, density, and temperature.

3. A device according to claim 1, wherein the sensor unit is chosen from the group consisting of capacitors, ultrasound sensors, pH electrodes, torque transducers, quartz oscillators, thermoelements, current meters, voltage meters, resistance meters, wire strain gauges, and force transducers.

4. A device according to claim 1, wherein the display unit can output at least one of a visual signal or an acoustic signal.

5. A device according to claim 1, wherein the sensor unit can record a change in torque applied to the mixer shaft.

6. A device according to claim 1 including means for determining the end of the processing time of hardening compounds.

7. A device according to claim 6, wherein the hardening compound is a dental impression compound.

8. A method for recording change and outputting a signal of change in a mixed and dispersed compound, comprising:
    a) mixing a hardening compound in a dynamic disposable mixer which is driven by a mixer-shaft motor;
    b) dispensing almost all of the compound from the dynamic disposable mixer;
    c) recording the change in at least one of the rheological properties of the mixed compound which remains in the dynamic disposable mixer via a sensor unit; and
    d) outputting a signal as soon as the value of the change from step c) has reached a predeterminable threshold value,
    wherein the sensor unit cooperates with the mixer-shaft motor.

9. A method according to claim 8, wherein at least step c) is performed with a device comprising:
    a mixer-shaft motor having a control;
    a mixer shaft;
    a seat for a cartridge which can be connected to a dynamic disposable mixer which is used to mix the hardening compound;
    a display unit; and
    a sensor unit which can record the change in at least one of the rheological properties of the compound,
    wherein the sensor unit is coupled to the mixer-shaft motor; and
    wherein the disposable mixer cooperates with the sensor unit.

10. A method according to claim 8, wherein the recording of step c) comprises recording a change in the torque applied to the mixer shaft.

11. A method according to claim 8, wherein the measurement in step c) is pulsed.

12. A method according to claim 8, wherein the measurement in step c) takes place with a speed of rotation which is smaller than the speed of rotation which is used in step a) for mixing.

13. A method according to claim 8, wherein the mixer shaft is not fully rotated during the measurement in step c).

14. A use of a method according to claim 8 for determining the end of the processing time of hardening compounds.

15. A use according to claim 14, wherein the hardening compound is a dental impression compound.

16. A dynamic disposable mixer device for mixing, dispensing and subsequently monitoring the setting profile of hardening compounds comprising:
   a mixer-shaft motor having a control;
   a mixer shaft;
   a sensor unit which can record the change in at least one of the rheological properties of the hardening compounds, wherein the sensor unit is coupled to the mixer-shaft motor;
   a display unit; and
   a dynamic disposable mixer which is configured to mix and dispense the hardening compounds, wherein the disposable mixer cooperates with the sensor unit to record the change in a rheological property of a portion of the hardening compound remaining in the mixer after a separate portion of the hardening compound has been dispensed.

17. The mixer device of claim 16, wherein the rheological properties are chosen from the group consisting of viscosity, compressive strength, pH, conductivity, dielectric constant, impedance, capacitance, hardness, density, and temperature.

18. The mixer device of claim 16, wherein the sensor unit is chosen from the group consisting of capacitors, ultrasound sensors, pH electrodes, torque transducers, quartz oscillators, thermoelements, current meters, voltage meters, resistance meters, wire strain gauges, and force transducers.

19. The mixer device of claim 16, wherein said display unit is configured to output at least one of a visual signal or an acoustic signal.

20. The mixer device of claim 16, wherein the sensor unit can detect a change in torque applied to the mixer shaft.

21. The mixer device of claim 16, including means for determining the end of the processing time of hardening compounds.

22. The mixer device of claim 16, wherein the sensor unit can detect the current consumption of the mixer-shaft motor.

* * * * *

UNITED STATES PATENT AND TRADEMARK OFFICE
CERTIFICATE OF CORRECTION

PATENT NO.    : 6,854,349 B2
DATED         : July 24, 2003
INVENTOR(S)   : Gerd Brandhorst It is certified that error appears in the above-identified patent and that said Letters Patent is hereby corrected as shown below:

<u>Title page,</u>
Item [75], Inventors, the listed inventor name "Mark Peuker" should be
-- Marc Peuker --

Signed and Sealed this

Seventeenth Day of May, 2005

JON W. DUDAS
*Director of the United States Patent and Trademark Office*